(12) United States Patent
Curley et al.

(10) Patent No.: US 8,408,210 B2
(45) Date of Patent: Apr. 2, 2013

(54) CUFFLESS TRACHEAL TUBE

(75) Inventors: James Curley, Offaly (IE); Brian Ledwith, Athlone (IE)

(73) Assignee: Covidien LP, Mansfield, MA (US)

( * ) Notice: Subject to any disclaimer, the term of this patent is extended or adjusted under 35 U.S.C. 154(b) by 552 days.

(21) Appl. No.: 12/642,174

(22) Filed: Dec. 18, 2009

(65) Prior Publication Data
US 2011/0146689 A1    Jun. 23, 2011

(51) Int. Cl.
*A61M 16/00* (2006.01)

(52) U.S. Cl. .................................. 128/207.15

(58) Field of Classification Search .............. 604/264, 604/96.01, 528, 533; 606/146, 114, 191–194; 128/207.15
See application file for complete search history.

(56) References Cited

U.S. PATENT DOCUMENTS

| | | | |
|---|---|---|---|
| 4,584,998 A * | 4/1986 | McGrail | 128/207.15 |
| 5,379,765 A | 1/1995 | Kajiwara et al. | |
| 6,679,836 B2 * | 1/2004 | Couvillon, Jr. | 600/146 |
| 6,960,163 B2 | 11/2005 | Ewers et al. | |
| 7,394,182 B2 | 7/2008 | Pelrine et al. | |
| 7,397,166 B1 | 7/2008 | Morgan et al. | |
| 7,566,297 B2 | 7/2009 | Banik | |
| 7,758,512 B2 * | 7/2010 | Swayze et al. | 600/528 |
| 7,909,844 B2 * | 3/2011 | Alkhatib et al. | 606/192 |
| 2004/0068224 A1 | 4/2004 | Couvillon et al. | |
| 2007/0038238 A1 | 2/2007 | Freeman et al. | |
| 2007/0049794 A1 | 3/2007 | Glassenberg et al. | |
| 2008/0047566 A1 | 2/2008 | Hegde et al. | |
| 2008/0078401 A1 | 4/2008 | Oneil et al. | |
| 2008/0078405 A1 | 4/2008 | Crumback et al. | |
| 2008/0086081 A1 | 4/2008 | Eidenschink et al. | |
| 2009/0159085 A1 | 6/2009 | Sleva | |

FOREIGN PATENT DOCUMENTS

WO    WO2008014028    1/2008

OTHER PUBLICATIONS

Creganna, Creganna acquire Micromuscle™ Technology,www.creganna.com/news.aspx?news_id=53, last viewed on Oct. 27, 2009.
Electroactive Polymer Technology Developed in Sweden Finds New Berth in Galway, http://medtechinsider.com/?p=4390, Blog Archive, last viewed on Oct. 27, 2009.
Actuator and Material Properties, www.micromuscle.com/applications/biomems/Micromuscle%20Technology%20Specifications.pdf, last viewed on Oct. 27, 2009.
International Search Report for PCT Application No. PCT/US2010/059808 dated Apr. 6, 2011, 10 pgs.

* cited by examiner

*Primary Examiner* — Manuel Mendez

(57) ABSTRACT

According to various embodiments, a tracheal tube ventilating device includes a sealing portion near a distal end of the tube. The sealing portion has an electroactive polymer configured to undergo a clinically effective change in volume, thickness, or both upon application of an electrical potential. Such a change in volume, thickness, or both enables sealing of the device against an inner surface of a trachea while permitting the free passage of ventilating gas through the tube. In addition, at least one electrical conductor is coupled to the electroactive polymer and is configured to apply the electrical potential.

30 Claims, 5 Drawing Sheets

CUFFLESS TRACHEAL TUBE

BACKGROUND

The present disclosure relates generally to medical devices and, more particularly, to airway devices, such as tracheal tubes.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, medical devices, such as tracheal tubes, may be used to control the flow of air or other gases through a trachea of a patient. Such tracheal tubes may include endotracheal tubes (ETTs), tracheotomy tubes, or transtracheal tubes. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient. In addition, a high-quality seal against the tracheal passageway allows a ventilator to perform efficiently.

Generally, tracheal tubes are available in a range of sizes from which doctors may select the closest approximate size for a particular patient. The differences between tube sizes may generally reflect both differences in the length of the tube as well as different tube diameters. In particular, doctors may wish to select a tracheal tube with an appropriate diameter in order to allow the tube to be easily inserted into the patient while providing the largest possible airway path for respiratory gases. For example, a tracheal tube with too small a tube diameter may result in a high pressure drop during breathing or ventilation. Conversely, a tracheal tube with too large a tube diameter can become difficult to navigate through the larynx and trachea, possibly increasing the time required to intubate the patient. In addition, a large tracheal tube can prove somewhat uncomfortable for the patient. For instance, irritation of the tracheal walls can result from increased contact with the tracheal tube.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
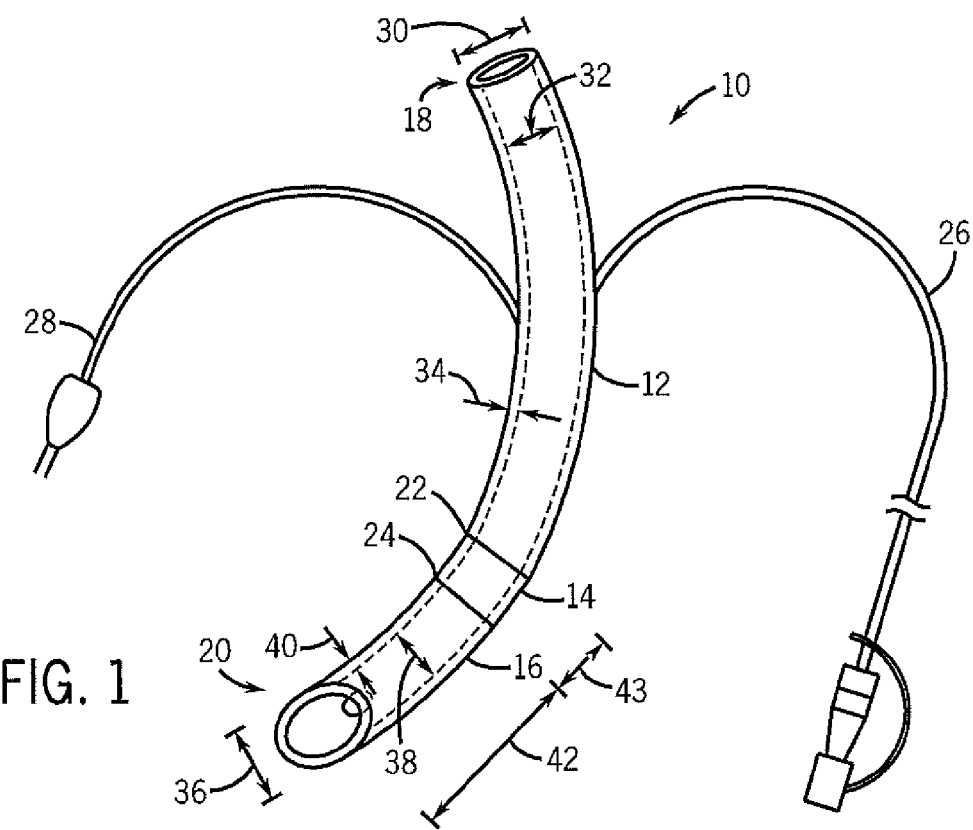
FIG. 1 is a perspective view of an exemplary ETT with a distal tip comprising electroactive polymer (EAP) in an unexpanded state.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A tracheal tube ventilating device may be used to seal an airway of a patient and provide positive pressure to the lungs when properly positioned in a trachea. The ventilating gas passing through the tube typically comprises air, but may also include anesthetic gases, medications, or various gas mixtures, such as mixtures containing higher concentrations of oxygen than atmospheric air. In addition, the source of the ventilating gas is typically a medical device such as a ventilator. During intubation or extubation, a clinician guides the tube through the upper respiratory tract and past the vocal cords. This opening is typically smaller than the inner diameter of the trachea. Thus, if possible, an outer diameter of the tube is minimized during intubation or extubation. Conversely, once the tube is properly positioned in the trachea, the tube outer diameter is increased enough to create a seal with the inner surface of the trachea. Finally, if possible, the tube inner diameter may be increased to provide less resistance to the flow of gas.

Electroactive polymers (EAP) are polymers having shapes that can be modified when an electric potential is applied to them. EAPs are generally divided into two categories: dielectric EAPs and ionic EAPs. Activation of dielectric EAPs occurs when electrostatic forces are created between two electrodes. The present techniques contemplate the use of ionic EAPs, which require electric potentials of only a few volts and electric currents in the range of a few microamps or milliamps, making them ideally suited for use in humans. Moreover, many ionic EAPs are biocompatible. Ionic EAPs swell and contract based on the movement of ions and water molecules into or out of the polymer. Reversing or removing the electric potential causes the ions and water molecules to move in the opposite direction. Thus, these unique materials offer the ability to control the size and/or shape of a portion of an ETT, as described below. In addition, devices comprising EAP can configured in a variety of ways to accomplish needed changes in volume, length, and/or diameter of the tube or a portion of the tube.

An EAP may be selected that undergoes a clinically effective change in volume, thickness, or both upon application of an electrical potential. For example, an EAP may undergo a change in volume, thickness, or both of at least approximately 20%. In other embodiments, the increase may be at least approximately 30%. Using such an EAP in a tracheal tube enables a tube to be designed that has a minimal outside diameter during intubation or extubation and an increased outside diameter sufficient to create a seal once properly positioned in the trachea. Using EAP provides the clinician with the ability to adjust the outside diameter just enough to create a proper seal. In addition, the inside diameter of the tube may also be increased subsequent to intubation to ease the flow of gases during patient ventilation. Further, as the outer walls of the tube may contact the trachea over its length, the length of the seal may be increased to provide improved sealing. Moreover, EAP will maintain its shape or volume as long as the proper electrical potential is maintained.

Various non-limiting examples of embodiments of tracheal tubes comprising EAP are disclosed below. For example, in certain embodiments, an entire portion of the tracheal tube may comprise EAP. In other embodiments, a layer of EAP may be disposed over the tube. Other configurations are possible as well. Thus, the clinician has the capability of adjusting the various dimensions of the tube to facilitate intubation and extubation, maintain a proper seal, provide maximum ventilation, and enhance patient comfort.

In certain embodiments, the disclosed tracheal tubes, systems, and methods may be used in conjunction with any appropriate medical device, including without limitation a feeding tube, an ETT, a tracheotomy tube, a circuit, an airway accessory, a connector, an adapter, a filter, a humidifier, a nebulizer, nasal cannula, or a supraglottic mask/tube. The present techniques may also be used to treat any patient benefiting from mechanical ventilation, e.g., positive pressure ventilation. Further, the devices and techniques provided herein may be used to treat human patients, such as trauma victims, patients with tracheotomies, anesthetized patients, cardiac arrest victims, patients suffering from airway obstructions, and patients suffering from respiratory failure.

FIG. 1 is a perspective view of an embodiment of an ETT 10 with a tip comprising an EAP in an unexpanded state. In the illustrated embodiment, the ETT 10 comprises a tubular body 12. The tubular body 12 comprises a proximal end 18 and a distal end 20. In addition, the tubular body 12 comprises a first material, a second material, and a transition region joining the two materials. Specifically, in certain embodiments, the first material used for the proximal end 18 of the tubular body 12 may be selected from materials commonly used for ETTs, such as polyvinyl chloride (PVC). A transition 14 to the EAP tip begins near the middle or distal end 20 of the tubular body 12. The transition 14 comprises a region where the first material used for the proximal end 18 of the tubular body 12 is gradually replaced by the EAP. In a presently contemplated embodiment, the second material used for the EAP section 16 of the tubular body 12 comprises substantially all EAP and almost none of the first material, although various mixtures of the materials that still provide the desired shape-changing properties may be employed. Examples of EAPs include, but are not limited to, polypyrroles, polyanilines, polythiphenes, polyethylenedisoxythiophenes, or mixtures thereof. Such EAPs are capable of undergoing a clinically effective change in volume, thickness, or both upon application of an electrical potential. As the second material used for the EAP section 16 may be less rigid than the first material used for the rest of the tubular body 12, a tool such as a stylet may be used to facilitate intubation. The transition 14 comprises a proximal side 22 and a distal side 24. The distal side is positioned towards the lower respiratory tract, while the proximal side is oppositely oriented.

Other elements of the ETT 10 may include a suction lumen 26 to remove secretions that may reside above the EAP section 16 during use. Further, at least one electrical conductor 28 couples the EAP section 16 to a source of electrical potential. In certain embodiments, the electrical conductor 28 may comprise a pair of insulated wires extending from the source of electrical potential, passing through a lumen of the tubular body 12, and emerging in the EAP as the bare ends of the wires, or small terminal plates or electrodes. Examples of sources of electrical potential include, but are not limited to, batteries, power supplies, wall current, generators, etc. The electrical conductor 28 may comprise a plug or other adaptor to enable it to be connected to the source of electrical potential. In certain embodiments, the electrical potential applied to the EAP may be between approximately 1 to 2 volts. Depending on the EAP and the direction of electric current, the electrical potential may act to expand or collapse the EAP.

Dimensions of the ETT 10 include an outside diameter 30 of the tubular body 12 at the proximal end 18. In certain embodiments, the outside diameter 30 at the proximal end 18 may be between approximately 2 and 16 mm. Further, the tubular body 12 near the proximal end 18 comprises an inside diameter 32. In certain embodiments, the inside diameter 32 near the proximal end 18 may be between approximately 1.5 and 12 mm. Thus, a wall thickness 34 of the tubular body 12 may be between approximately 0.5 to 2 mm. The EAP section 16 also comprises an unexpanded outside diameter 36, an inside diameter 38, and an unexpanded wall thickness 40. In certain embodiments, the dimensions of the EAP section 16 when unexpanded may be substantially the same as the dimensions of the proximal end 18 of the tubular body 12. Finally, the EAP section 16 may comprise a length 42 configured to be long enough to allow the EAP section 16 to create a sufficient seal against the trachea wall. In certain embodiments, the EAP length 42 may be between approximately 8 and 50 mm. The transition 14 may comprise a length 43 configured to be long enough to enable standard tube manufacturing techniques to transition from the first material to the second material in as short a distance as possible. In certain embodiments, the transition length 43 may be between approximately 10 and 20 mm.

Figure 2:
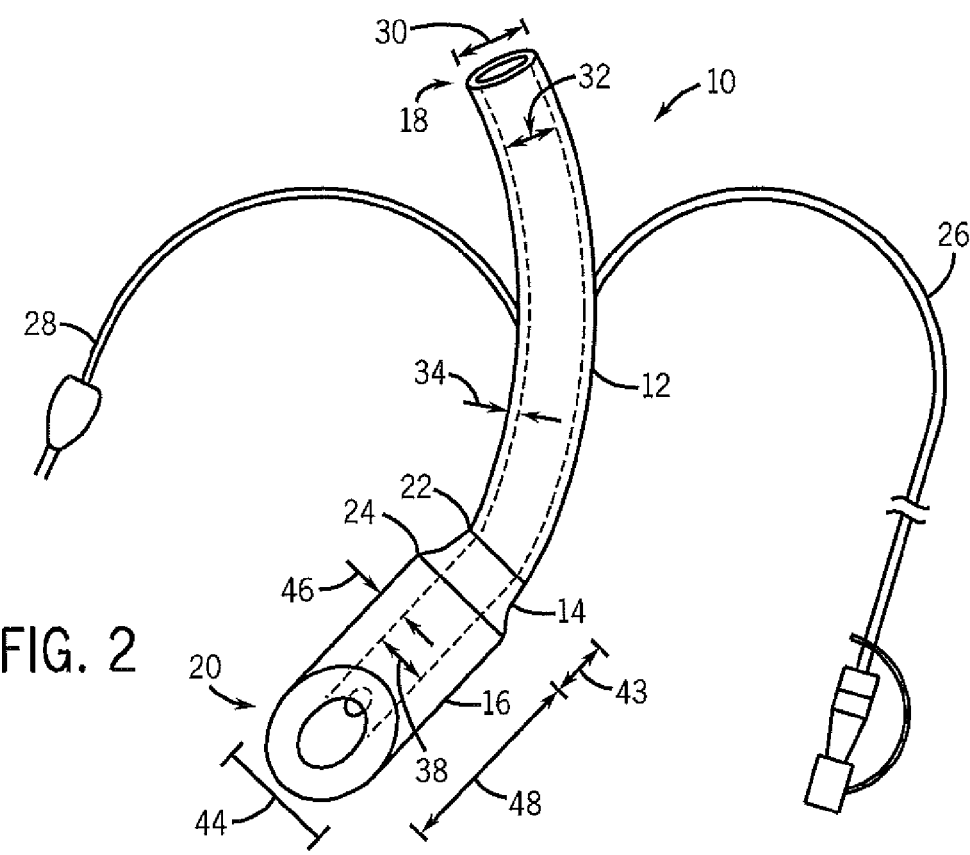
FIG. 2 is a perspective view of an exemplary ETT with a distal tip comprising EAP in an expanded state.

FIG. 2 is a perspective view of an embodiment of an ETT 10 with a tip comprising an EAP in an expanded state. In the illustrated embodiment, the expanded EAP section 16 comprises an outside diameter 44, a wall thickness 46, and a length 48. In certain embodiments, the expanded outside diameter 44 may be between approximately 8 and 55 mm. For example, the expanded outside diameter 44 of the EAP section 16 may be at least approximately 20% greater than the unexpanded diameter 36 of the EAP section 16. In other embodiments, the increase may be at least approximately 30%. The expanded outside diameter 44 is configured to be large enough to allow the EAP section 16 to create an effective seal against the trachea wall. In certain embodiments, the expanded wall thickness 46 of the EAP section 16 may be between approximately 2 and 8 mm. Although most of the expansion of the EAP may be configured to contribute to an increased wall thickness of the EAP section 16, there may be some increase in the length of the EAP section as well. In certain embodiments, the expanded length 48 of the EAP section 16 may be between approximately 8 and 55 mm. In the particular embodiment shown, because the transition 14 comprises some EAP, it may expand an amount less than the EAP section 16. In addition, the inside diameter 38 of the EAP section 16 remains the same in the expanded state, as substantially all of the expansion of the EAP in this embodiment is directed outward. Other elements shown in FIG. 2 in common with those shown in FIG. 1 are discussed above.

Figure 3:
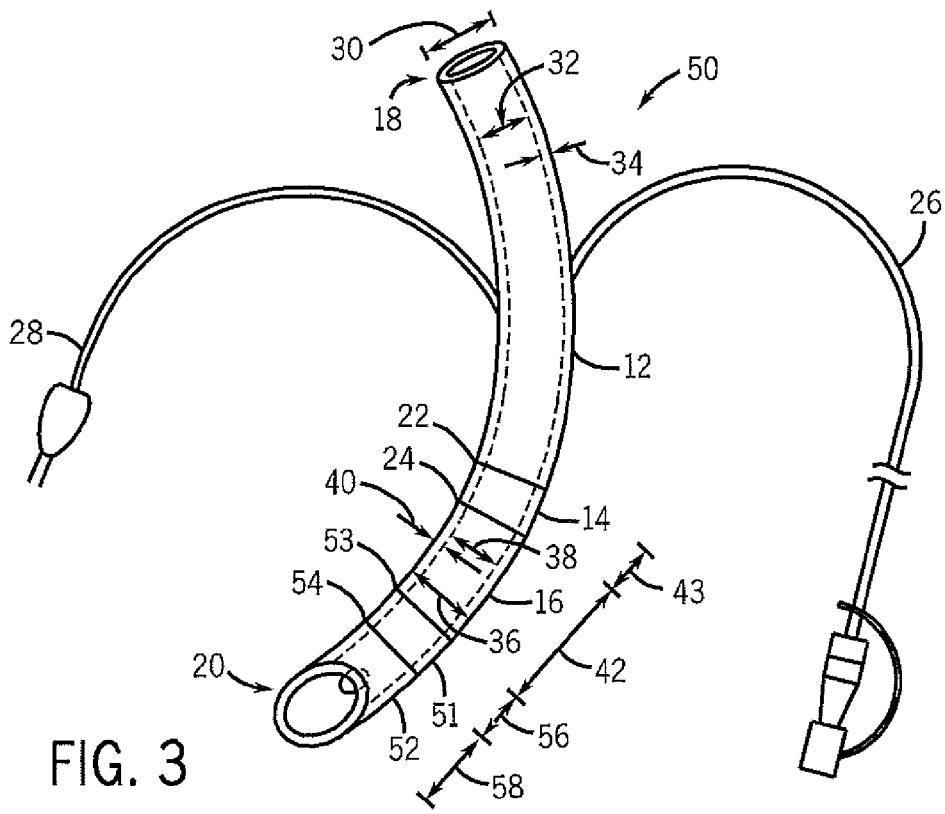
FIG. 3 is a perspective view of an exemplary ETT with an EAP middle section in an unexpanded state.

FIG. 3 is a perspective view of an embodiment of an ETT 50 with an EAP middle section 16 in an unexpanded state. In the illustrated embodiment, because the EAP section 16 is in the middle of a tubular body 12, the body comprises two transition sections: a proximal transition 14 and a distal transition 51. The distal transition 51 comprises a proximal side 53 and a distal side 54. In addition, the distal transition 51 comprises a length 56. In certain embodiments, the distal transition length 56 may be the same as the proximal transition length 43, such as between approximately 10 and 20 mm. The tubular body 12 comprises a distal tip 52 that does not comprise EAP. Instead, the non-EAP distal tip 52 may be comprised of the same or similar materials as the proximal end of the tubular body 12, such as, but not limited to PVC. The non-RAP distal tip 52 comprises a length 58 that may be configured to be long enough such that the EAP section 16 is located an anatomically relevant distance from the distal end of the tubular body 12. In certain embodiments, the length 58 of the non-EAP distal tip 52 may be between approximately 3 and 20 mm. Other elements shown in FIG. 3 in common with those shown in FIG. 1 are discussed above.

Figure 4:
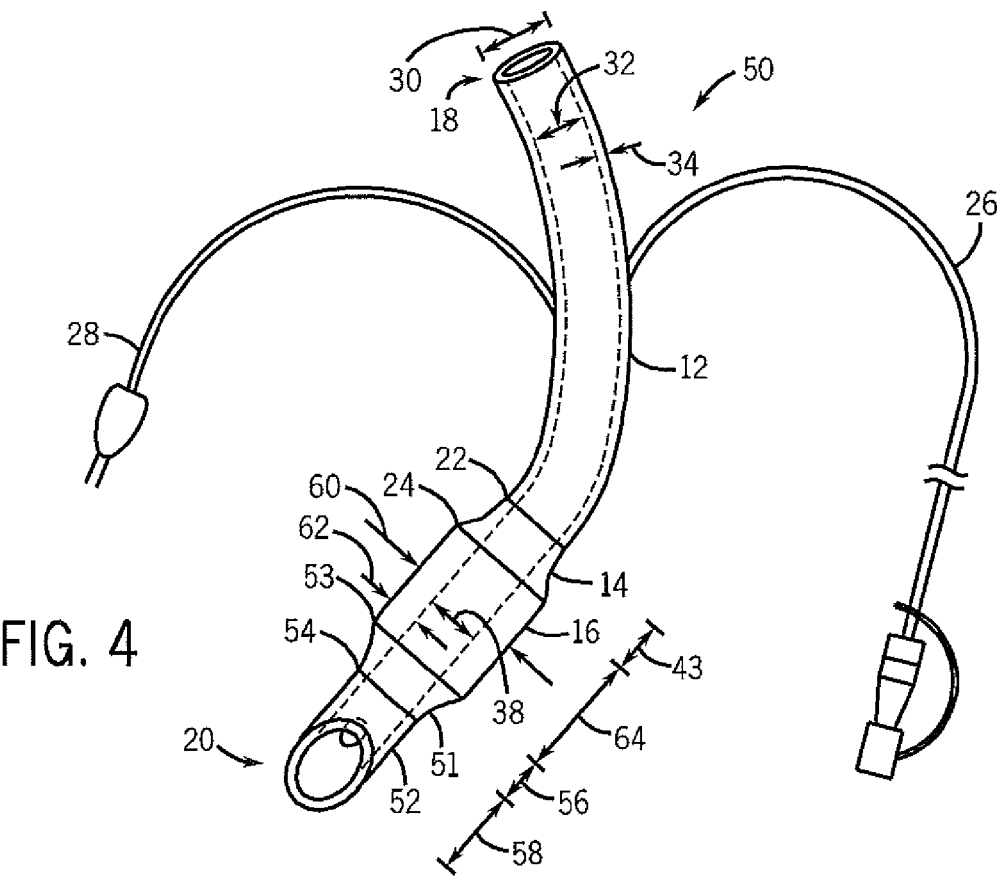
FIG. 4 is a perspective view of an exemplary ETT with an EAP middle section in an expanded state.

FIG. 4 is a perspective view of an embodiment of an ETT 50 with an EAP middle section 16 in an expanded state. In the illustrated embodiment, the expanded EAP section 16 comprises an outside diameter 60, a wall thickness 62, and a length 64. In certain embodiments, the expanded outside diameter 60 may be between approximately 8 and 55 mm. For example, the expanded outside diameter 60 of the EAP section 16 may be at least approximately 20% greater than the unexpanded diameter 36 of the EAP section 16. In other embodiments, the increase may be at least approximately 30%. The expanded outside diameter 60 is configured to be large enough to allow the EAP section 16 to create an effective seal against the trachea wall. In certain embodiments, the expanded wall thickness 62 of the EAP section 16 may be between approximately 2 and 8 mm. Although most of the expansion of the EAP may be configured to contribute to an increased wall thickness of the EAP section 16, there may be some increase in the length of the EAP section as well. In certain embodiments, the expanded length 64 of the EAP section 16 may be between approximately 8 and 55 mm. In the particular embodiment shown, because the proximal transition 14 and the distal transition 51 both comprise some EAP, they may expand an amount less than the EAP section 16. In addition, the inside diameter 38 of the EAP section 16 remains the same in the expanded state, as substantially all of the expansion of the EAP in this embodiment is directed outward. Other elements shown in FIG. 4 in common with those shown in FIG. 3 are discussed above.

Figure 5:
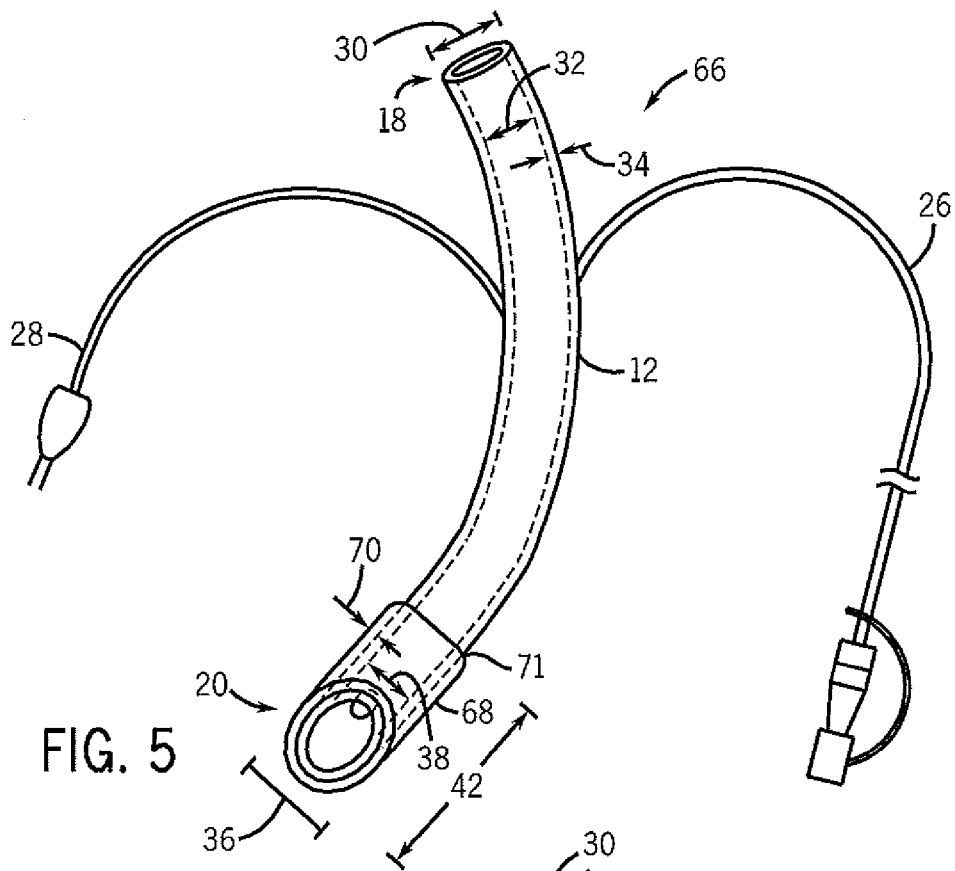
FIG. 5 is a perspective view of an exemplary ETT with an outer layer of EAP in an unexpanded state disposed on an outer surface of the tube.

FIG. 5 is a perspective view of an embodiment of an ETT 66 with an outer layer of EAP 68 in an unexpanded state disposed over the tubular body 12. Such a configuration offers an alternative method of construction compared to the ETTs discussed above, but still employs EAP as the sealing material. In the illustrated embodiment, the EAP layer 68 comprises a thickness 70, configured to be small enough to enable the ETT 66 to be easily intubated or extubated. In certain embodiments, the thickness 70 of the EAP layer 68 may be between approximately 0.5 to 1 mm. An interface 71 exists where the EAP layer 68 begins on the tubular body 12. Other elements shown in FIG. 5 in common with those shown in FIG. 1 are discussed above.

Figure 6:
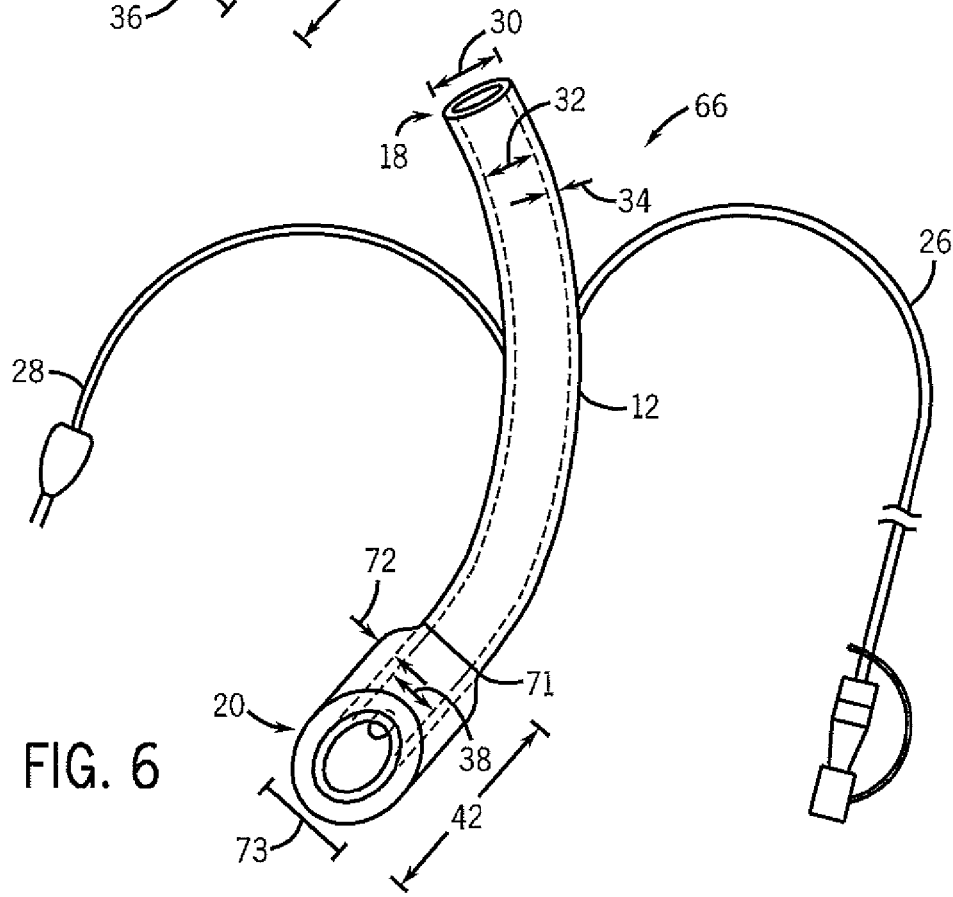
FIG. 6 is a perspective view of an exemplary ETT with an outer layer of EAP in an expanded state disposed on an outer surface of the tube.

FIG. 6 is a perspective view of an embodiment of an ETT 66 with an EAP layer 68 in an expanded state. In the illustrated embodiment, the expanded EAP layer 68 comprises a wall thickness 72 and an outside diameter 73. In certain embodiments, the expanded wall thickness 72 of the EAP layer 68 may be between approximately 2 and 8 mm. As the expansion of the EAP layer 68 inward is limited by the tubular body 12, substantially all the growth is directed outward. In certain embodiments, the expanded outside diameter 73 of the EAP layer 68 may be between approximately 8 and 55 mm. For example, the expanded outside diameter 73 of the EAP layer 68 may be at least approximately 20% greater than the unexpanded diameter 36 of the EAP layer 68. In other embodiments, the increase may be at least approximately 30%. The expanded outside diameter 73 is configured to be large enough to allow the EAP layer 68 to create an effective seal against the trachea wall. Other elements shown in FIG. 6 in common with those shown in FIG. 5 are discussed above.

Figure 7:
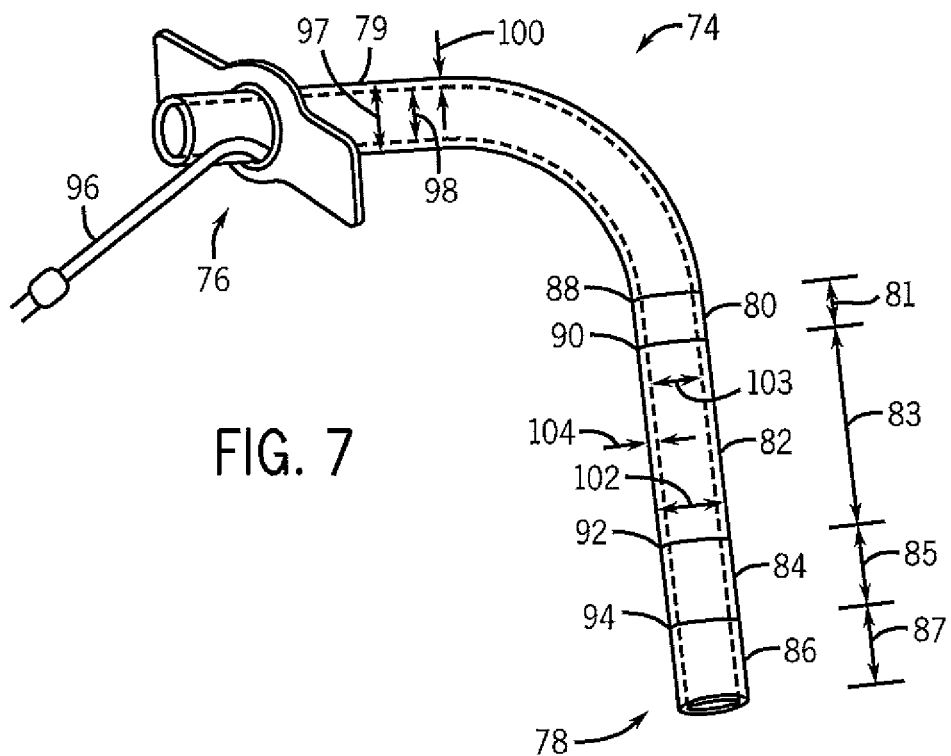
FIG. 7 is a perspective view of an exemplary tracheostomy tube with an EAP middle section in an unexpanded state.

FIG. 7 is a perspective view of an embodiment of a tracheostomy tube 74 with an EAP middle section 82 in an unexpanded state. In the illustrated embodiment, the tube 74 comprises a proximal end 76 and a distal end 78. Because the EAP section 82 is in the middle of the tube 74, the tube comprises two transition sections: a proximal transition 80 and a distal transition 84. The proximal transition 80 comprises a length 81 and the distal transition comprises a length 85. In certain embodiments, the proximal transition length 81 and the distal transition length 85 may be the same, such as between approximately 10 and 20 mm. The proximal transition 80 comprises a proximal side 88 and a distal side 90. Similarly, the distal transition 84 comprises a proximal side 92 and a distal side 94. In addition, the EAP section 82 comprises a length 83. In certain embodiments, the EAP length 83 may be between approximately 8 and 55 mm. The tube 74 comprises a distal tip 86 that does not comprise EAP. Instead, the non-RAP distal tip 86 may be comprised of the same or similar materials as the proximal end of the tube 74, such as, but not limited to PVC. The non-EAP distal tip 86 comprises a length 87 that may be configured to be long enough such that the EAP section 82 is located an anatomically relevant distance from the distal end of the tube 74. In certain embodiments, the length 87 of the non-EAP distal tip 86 may be approximately 3 and 20 mm.

Other elements of the tube 74 include at least one electrical conductor 96 that couples the EAP section 82 to a source of electrical potential. In certain embodiments, the electrical potential applied to the EAP may be between approximately 1 to 2 volts. Dimensions of the tube 74 near the proximal end 76 include an outside diameter 97, an inside diameter 98, and a wall thickness 100. In certain embodiments, the outside diameter 97 at the proximal end 18 may be between approximately 2 and 16 mm, the inside diameter 98 may be between approximately 1.5 and 12 mm, and the wall thickness 100 may be between approximately 0.5 and 2 mm. The EAP section 82 also comprises an unexpanded outside diameter 102, an inside diameter 103, and a wall thickness 104. In certain embodiments, the dimensions of the EAP section 82 when unexpanded may be substantially the same as the dimensions of the proximal end 76 of the tube 74. Other features of the tube 74 analogous to ETTs are discussed above.

Figure 8:
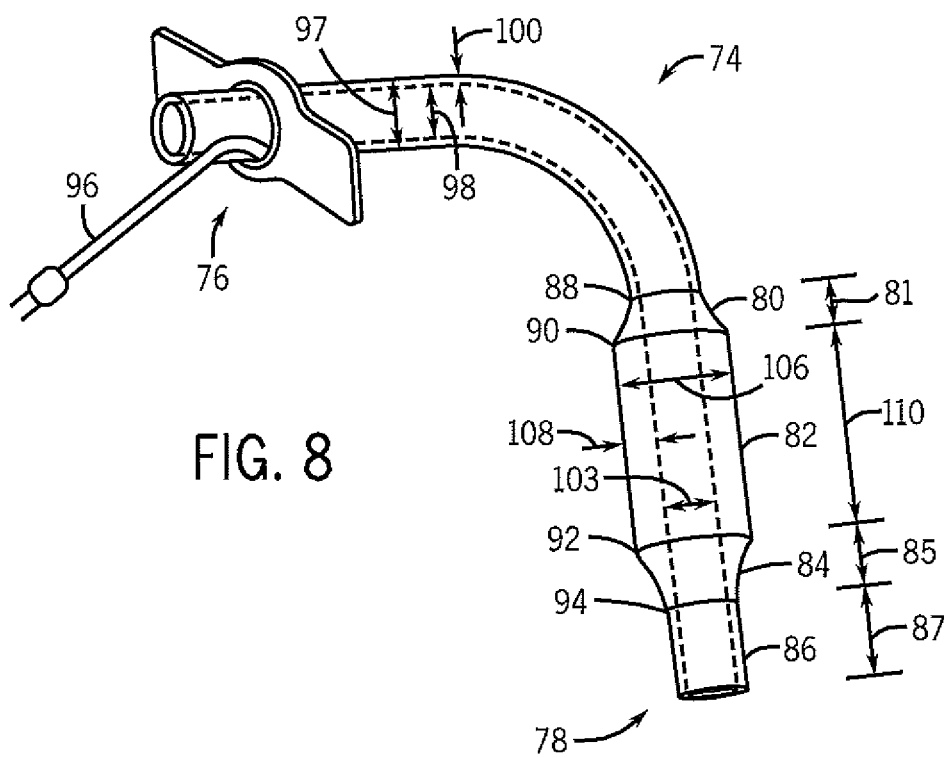
FIG. 8 is a perspective view of an exemplary tracheostomy tube with an EAP middle section in an expanded state.

FIG. 8 is a perspective view of an embodiment of a tube 74 with an EAP middle section 82 in an expanded state. In the illustrated embodiment, the expanded EAP section 82 comprises an outside diameter 106, a wall thickness 108, and a length 110. In certain embodiments, the expanded outside diameter 60 may be between approximately 8 and 55 mm. For example, the expanded outside diameter 106 of the EAP section 82 may be at least approximately 20% greater than the unexpanded diameter 102 of the EAP section 82. In other embodiments, the increase may be at least approximately 30%. The expanded outside diameter 106 is configured to be large enough to allow the EAP section 82 to create an effective seal against the trachea wall. In certain embodiments, the expanded wall thickness 108 of the EAP section 82 may be between approximately 2 and 8 mm. Although most of the expansion of the EAP may be configured to contribute to an increased wall thickness of the EAP section 82, there may be some increase in the length of the EAP section as well. In certain embodiments, the expanded length 110 of the EAP section 82 may be between approximately 8 and 55 mm. In the particular embodiment shown, because the proximal transition 80 and the distal transition 84 both comprise some EAP, they may expand an amount less than the EAP section 82. In addition, the inside diameter 103 of the EAP section 82 remains the same in the expanded state, as substantially all of the expansion of the EAP is directed outward. Other elements shown in FIG. 8 in common with those shown in FIG. 7 are discussed above.

Figure 9:
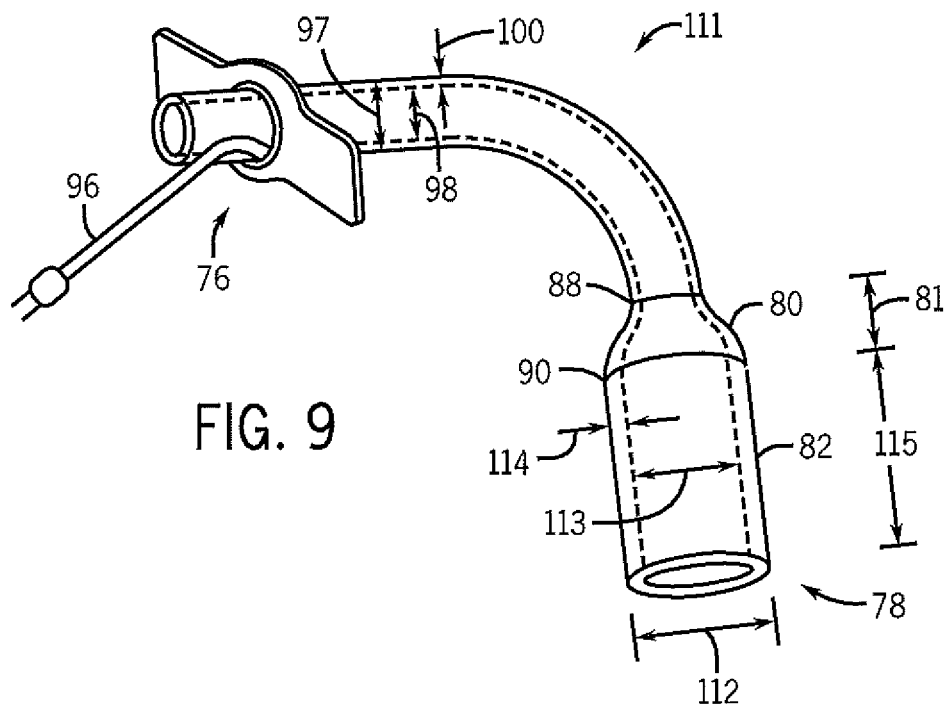
FIG. 9 is a perspective view of an exemplary tracheostomy tube with a distal tip comprising EAP in an expanded state.

FIG. 9 is a perspective view of an embodiment of a tracheostomy tube 111 with a tip comprising EAP 82 in an expanded state. In the illustrated embodiment, the expanded EAP section 82 comprises an outside diameter 112, an inside diameter 113, a wall thickness 114, and a length 115. Although similar in appearance to the expanded ETT shown in FIG. 2, the EAP section 82 in FIG. 9 is configured to not only increase the outside diameter 112, but also the inside diameter 113 in the expanded state. An increased inside diameter may reduce the resistance of air passing through the tube, increasing ventilation to the patient. This may be accomplished by advantageous arrangement of the EAP material within the EAP section 82. This feature may also be employed in the ETTs shown in FIGS. 1-4 and the tracheostomy tubes shown in FIGS. 7 and 8 discussed above. In certain embodiments, the expanded inside diameter 113 may be between approximately 6 and 53 mm. In certain embodiments, the expanded outside diameter 112 may be between approximately 8 and 55 mm, the expanded wall thickness 114 may between approximately 2 and 8 mm, and the expanded length 115 may be between approximately 8 and 55 mm. The expanded outside diameter 112 is configured to be large enough to allow the EAP section 82 to create an effective seal against the trachea wall. Other elements shown in FIG. 9 in common with those shown in FIG. 7 are discussed above.

Figure 10:
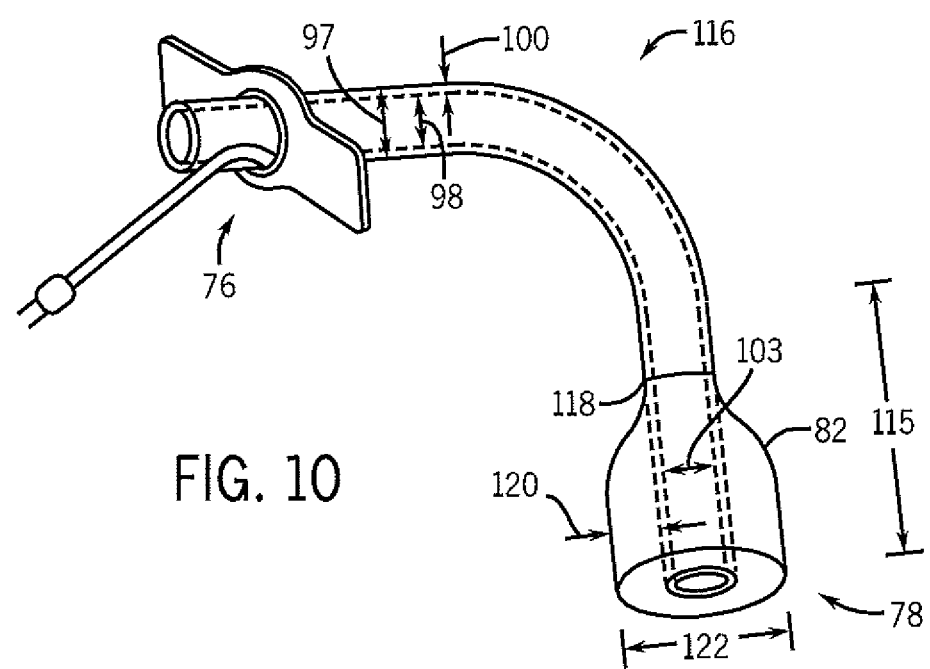
FIG. 10 is a perspective view of an exemplary tracheostomy tube with an outer layer of EAP in an expanded state disposed on an outer surface of the tube.

FIG. 10 is a perspective view of an embodiment of a tracheostomy tube 116 with an outer layer of EAP 82 in an expanded state disposed over the tube. In the illustrated embodiment, an interface 118 exists where the EAP layer 82 begins on the tube 116. In addition, the expanded EAP section 82 comprises a wall thickness 120 and an outside diameter 122. In certain embodiments, the expanded wall thickness 120 of the EAP layer 82 may be between approximately 2 and 8 mm. As the expansion of the EAP layer 82 inward is limited by the tube 116, substantially all the growth is directed outward. In certain embodiments, the expanded outside diameter 122 of the EAP layer 82 may be between approximately 8 and 55 mm. For example, the expanded outside diameter 122 of the EAP layer 82 may be approximately 20% greater than the unexpanded diameter of the EAP layer 82. In other embodiments, the increase may be at least approximately 30%. The expanded outside diameter 122 is configured to be large enough to allow the EAP layer 82 to create an effective seal against the trachea wall. Other elements shown in FIG. 10 in common with those shown in FIG. 7 are discussed above.

What is claimed is:

1. A tracheal tube ventilating device comprising:
   a tubular body configured to be inserted into the trachea of a patient and comprising a single generally annular sealing portion, wherein the generally annular sealing portion at or near a distal end of the tubular body comprises an electroactive polymer configured to undergo a clinically effective change in volume, thickness, or both upon application of an electrical potential to seal against an inner surface of the trachea while permitting the free passage of ventilating gas therethrough, the generally annular sealing portion having a central passage for conveying gas to and from the lungs, and wherein the central passage remains open when the electroactive polymer undergoes the clinically effective change in volume, thickness, or both; and
   at least one electrical conductor coupled to the electroactive polymer and configured to apply the electrical potential.

2. The tracheal tube ventilating device of claim 1, wherein the clinically effective change in volume, thickness, or both causes a change in an outside diameter of the sealing portion, a change in an inside diameter of the sealing portion, or a combination thereof.

3. The tracheal tube ventilating device of claim 2, wherein the outside diameter undergoes a change of at least approximately 20% when the electrical potential is applied to the electroactive polymer.

4. The tracheal tube ventilating device of claim 3, wherein the outside diameter undergoes a change of at least approximately 30% when the electrical potential is applied to the electroactive polymer.

5. The tracheal tube ventilating device of claim 2, wherein the outside diameter undergoes a change sufficient to create an effective seal against the inner surface of the trachea.

6. The tracheal tube ventilating device of claim 1, wherein the distal end of the tubular body comprises the sealing portion and the sealing portion comprises entirely electroactive polymer.

7. The tracheal tube ventilating device of claim 1, wherein the sealing portion comprises a length of about 8 to 55 millimeters.

8. The tracheal tube ventilating device of claim 1, wherein the sealing portion is located an anatomically relevant distance from the distal end of the tubular body and the sealing portion comprises entirely electroactive polymer.

9. The tracheal tube ventilating device of claim 1, wherein the distal end of the tracheal tube comprises the sealing portion and an outer layer of the electroactive polymer is disposed on the tubular body.

10. The tracheal tube ventilating device of claim 1, wherein the sealing portion is located an anatomically relevant distance from the distal end of the tubular body and an outer layer of the electroactive polymer is disposed on the tubular body.

11. The tracheal tube ventilating device of claim 1, wherein the tubular body is operatively connected to a ventilator.

12. The tracheal tube ventilating device of claim 1, wherein the electroactive polymer is selected from the group consisting of polypyrroles, polyanilines, polythiphenes, polyethylenedisoxythiophenes and mixtures thereof.

13. The tracheal tube ventilating device of claim 1, wherein the clinically effective change in volume, thickness or both is at least approximately 20%.

14. The tracheal tube ventilating device of claim 13, wherein the clinically effective change in volume, thickness or both is at least approximately 30%.

15. The tracheal tube ventilating device of claim 1, wherein the electric potential is about 1 to 2 volts.

16. The tracheal tube ventilating device of claim 1, wherein the tubular body comprises a first material;
wherein the electroactive polymer comprises a second material; and
further comprising a transition region joining the tubular body with the electroactive polymer.

17. The tracheal tube ventilating device of claim 1, further comprising a lumen, wherein the at least one electrical conductor is disposed inside the lumen.

18. A tracheal tube ventilating device comprising:
a tubular body configured to be inserted into the trachea of a patient and comprising a single generally annular sealing portion, wherein the generally annular sealing portion located an anatomically relevant distance from the distal end of the tubular body comprises an electroactive polymer layer disposed on the tubular body, wherein the electroactive polymer is configured to undergo a clinically effective change in volume, thickness, or both upon application of an electrical potential to seal against an inner surface of the trachea while permitting the free passage of ventilating gas therethrough, the generally annular sealing portion having a central passage for conveying gas to and from the lungs, and wherein the central passage remains open when the electroactive polymer undergoes the clinically effective change in volume, thickness, or both; and
at least one electrical conductor coupled to the electroactive polymer and configured to apply the electrical potential.

19. The tracheal tube ventilating device of claim 18, wherein the clinically effective change in volume, thickness, or both causes a change in an outside diameter of the sealing portion.

20. The tracheal tube ventilating device of claim 19, wherein the outside diameter undergoes a change of at least approximately 20% when the electrical potential is applied to the electroactive polymer.

21. The tracheal tube ventilating device of claim 20, wherein the outside diameter undergoes a change of at least approximately 30% when the electrical potential is applied to the electroactive polymer.

22. The tracheal tube ventilating device of claim 19, wherein the outside diameter undergoes a change sufficient to create an effective seal against the inner surface of the trachea when the electrical potential is applied to the electroactive polymer.

23. The tracheal tube ventilating device of claim 18, wherein the sealing portion comprises a length of about 8 to 55 millimeters.

24. The tracheal tube ventilating device of claim 18, wherein the tubular body is operatively connected to a ventilator.

25. The tracheal tube ventilating device of claim 18, wherein the electroactive polymer is selected from the group consisting of polypyrroles, polyanilines, polythiphenes, polyethylenedisoxythiophenes and mixtures thereof.

26. The tracheal tube ventilating device of claim 18, wherein the clinically effective change in volume, thickness or both is at least approximately 20%.

27. The tracheal tube ventilating device of claim 26, wherein the clinically effective change in volume, thickness or both is at least approximately 30%.

28. The tracheal tube ventilating device of claim 18, wherein the electric potential is about 1 to 2 volts.

29. The tracheal tube ventilating device of claim 18, further comprising a lumen, wherein the at least one electrical conductor is disposed inside the lumen.

30. A tracheal tube ventilating device comprising:
a tubular body configured to be inserted into the trachea of a patient and comprising a single generally annular sealing portion, wherein the generally annular sealing portion located an anatomically relevant distance from the distal end of the tubular body comprises an electroactive polymer layer disposed on the tubular body, wherein the electroactive polymer is configured to undergo a clinically effective change in volume, thickness, or both of at least approximately 20% upon application of an electrical potential to seal against an inner surface of the trachea while permitting the free passage of ventilating gas therethrough, the generally annular sealing portion having a central passage for conveying gas to and from the lungs, and wherein the central passage remains open when the electroactive polymer undergoes the clinically effective change in volume, thickness, or both;
at least one electrical conductor coupled to the electroactive polymer and configured to apply the electrical potential;
wherein the clinically effective change in volume, thickness, or both causes a change in an outside diameter of the sealing portion sufficient to create an effective seal against the inner surface of the trachea when the electrical potential is applied to the electroactive polymer;
wherein the sealing portion comprises a length of about 8 to 55 millimeters;
wherein the tubular body is operatively connected to a ventilator;
wherein the electroactive polymer is selected from the group consisting of polypyrroles, polyanilines, polythiphenes, polyethylenedisoxythiophenes and mixtures thereof;
wherein the electric potential is about 1 to 2 volts; and
further comprising a lumen, wherein the at least one electrical conductor is disposed inside the lumen.

* * * * *